(12) United States Patent
Zhang

(10) Patent No.: US 11,450,105 B2
(45) Date of Patent: Sep. 20, 2022

(54) SCALABLE SPORT DATA COLLECTING, SHARING AND PROCESSING SYSTEM

(71) Applicant: Hanhui Zhang, Clarksburg, MD (US)

(72) Inventor: Hanhui Zhang, Clarksburg, MD (US)

( * ) Notice: Subject to any disclaimer, the term of this patent is extended or adjusted under 35 U.S.C. 154(b) by 0 days.

(21) Appl. No.: 17/236,224

(22) Filed: Apr. 21, 2021

(65) Prior Publication Data

US 2021/0334546 A1 Oct. 28, 2021

Related U.S. Application Data

(60) Provisional application No. 63/014,188, filed on Apr. 23, 2020.

(51) Int. Cl.
| | |
|---|---|
| *H04N 21/85* | (2011.01) |
| *G06V 20/40* | (2022.01) |
| *G06F 3/01* | (2006.01) |
| *H04N 21/81* | (2011.01) |

(52) U.S. Cl.
CPC .............. *G06V 20/42* (2022.01); *G06F 3/011* (2013.01); *H04N 21/8126* (2013.01); *H04N 21/85* (2013.01); *G06V 2201/07* (2022.01)

(58) Field of Classification Search
CPC ............................ G06F 3/011; H04N 21/8126
See application file for complete search history.

(56) References Cited

U.S. PATENT DOCUMENTS

| | | | |
|---|---|---|---|
| 2014/0063054 A1* | 3/2014 | Osterhout | G06F 3/005 345/633 |
| 2017/0146644 A1* | 5/2017 | Tucker | G02B 27/0172 |

* cited by examiner

*Primary Examiner* — Jerry T Jean Baptiste
(74) *Attorney, Agent, or Firm* — SZDC Law P.C.

(57) ABSTRACT

A scalable sport data collecting, sharing and processing system includes: a hub device, and a plurality of client devices, the client devices being connected to the hub device via a data communication link. The client devices include a producer client device and a consumer client device; the producer client device includes one or more sensors selected from the group consisting of be an image sensor, an audio sensor, a GPS/GNSS receiver, an accelerometer, a gyroscope, and a magnetometer, a processor, and a communication module; and the consumer client device includes a process, a communication module, a display and a data storage.

17 Claims, 6 Drawing Sheets

SCALABLE SPORT DATA COLLECTING, SHARING AND PROCESSING SYSTEM

This application claims priority to U.S. Provisional Patent Application No. 63/014,188, filed on Apr. 23, 2020, which is incorporated by reference for all purposes as if fully set forth herein.

FIELD OF THE INVENTION

The present application relates to a scalable sport data collecting, sharing and processing system.

BACKGROUND OF THE INVENTION

There are great interest and needs in collecting, sharing and processing sport data. The collection, share and process of sport data in real time in an automatic and efficient way will have broad applications in various sport events. The present applicant provides a scalable sport data collecting, sharing and processing system to meet such needs.

SUMMARY OF THE INVENTION

In one embodiment, the present application provides a scalable sport data collecting, sharing and processing system that includes: a hub device, and a plurality of client devices, each client device being connected to the hub device via a data communication link. The client devices include a producer client device and a consumer client device; the producer client device includes one or more sensors selected from the group consisting of be an image sensor, an audio sensor, a GPS/GNSS receiver, an accelerometer, a gyroscope, and a magnetometer, a processor, and a communication module; and the consumer client device includes a process, a communication module, a display and a data storage.

In another embodiment, the client devices further include a producer-consumer client device, and the producer-consumer client device includes one or more sensors selected from the group consisting of be an image sensor, an audio sensor, a GPS/GNSS receiver, an accelerometer, a gyroscope, and a magnetometer, a processor, a communication module, and a data storage.

In another embodiment, the producer client device generates and sends sport data packets to the hub; and the consumer client device receives and processes the sports data packets forwarded by the hub.

In another embodiment, the data communication link includes a data sharing logical channel, and the client devices are adapted for exchanging sport data with each other using the hub device as a router.

In another embodiment, the hub device includes a master timer, and the client devices each have a local timer that synchronizes with the master timer.

In another embodiment, a time synchronization is achieved and maintained by the hub broadcasting synchronization messages to the client devices or by two-way time synchronization messages exchanging between the hub and the client devices.

In another embodiment, the producer client device is a wearable sensor device that include sensors to measure the location, speed, acceleration, orientation of a wearing player.

In another embodiment, the wearable sensor device further includes a computing module, a battery, and a radio, and the sensors of the wearable sensor device include an accelerometer, a gyroscope, and a magnetometer.

In another embodiment, the producer client device is a device attached to a sport equipment that includes sensors to measure the location, speed, acceleration, orientation of the sport equipment.

In another embodiment, the producer client includes one or more image sensors and an image processer.

In another embodiment, the producer client includes a camera.

In another embodiment, the client devices are a smart phone.

In another embodiment, the data communication link between the producer client device and the hub device includes: sending a channel setup request from the producer client device to the hub, acknowledging the channel setup request by the hub, and sending sport data packets from the producer client device to the hub.

In another embodiment, the data communication link between the consumer client device and the hub device includes: sending a first channel subscription request from the consumer client device to the hub, sending a channel list by the hub to the consumer client device, sending a second channel subscription request from the consumer client device to the hub, acknowledging the second channel subscription request by the hub, and sending sport data packets from the hub to the consumer client device.

In another embodiment, the hub includes a database that includes client registration information, channel registration information, and channel subscriber information.

In another embodiment, the hub receives sport data packets from the producer client device, locates corresponding channel subscriber information, attaches additional information to the sport data packets from the database, and forwarding the sport data packets to the consumer client device.

In another embodiment, the scalable sport data collecting, sharing and processing system includes: an audience input client device, a wearable client device, a hub device, a referee input client device, a statistics display client device, and a camera client device; and the wearable client device generate sport data packets, the consumer client or the hub detects sports events by correlating the sport data packets, and the sport events are saved locally or encapsulated in new sport data packets and sent to the hub device.

In another embodiment, the hub device correlates the sport data packets with a first video clip recorded by the camera client device.

In another embodiment, the audience input client device generates a clip generation command, and the hub device correlates the clip generation command with a second video clip recorded by the camera client device.

In another embodiment, the producer client device generates sport data packets, the sport data packets encapsulate data collected from the sensors and a timestamp indicating the producer client device's local timer value when the sport data packets are generated; and the sport data packets are generated periodically or when the producer client device detects certain events.

It is to be understood that both the foregoing general description and the following detailed description are exemplary and explanatory and are intended to provide further explanation of the invention as claimed.

DETAILED DESCRIPTION

Reference will now be made in detail to embodiments of the present invention, example of which is illustrated in the accompanying drawings.

A scalable network for collecting, sharing and processing sports data is presented. A hub setup a centralized wire or wireless network with multiple client devices. The hub serves as the data router to route sport activity related data packets among said multiple client devices. Each client device has the capabilities of setting up the communication connection with said hub autonomously. After the communication connection is established, the client devices can share the sports data generated within the network.

Figure 1:
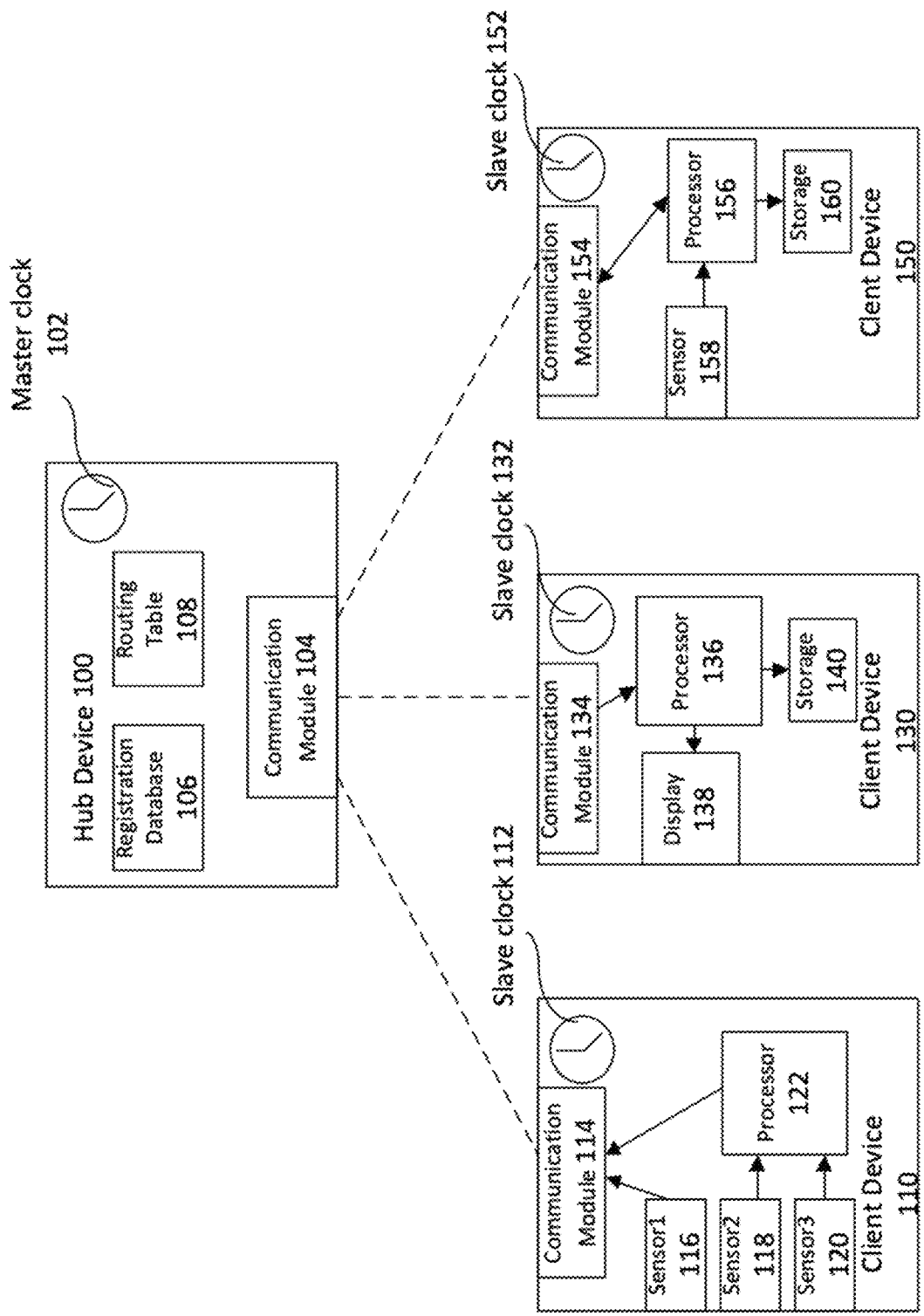
FIG. 1 illustrates a block diagram of a scalable sport data collecting, sharing and processing system.

FIG. 1 illustrates a block diagram of the present invention. A hub 100 establishes a centralized local network. Client devices 110, 130, 150 can setup wired or wireless data communication links with the hub 100 autonomously according certain authentication procedure. The communication links are shown as dash lines in FIG. 1. The data sharing logical channels then can be configured over the data communication links through the registration procedures. Once said logical channels established, the client device will be able to exchange sport related data with the other client devices using the hub 100 as a router.

For the preferred embodiments, the hub 100 and client devices 110, 130, 150 each have a local timer. The timer 102 in the hub 100 act as the master timer (master clock), which means the client devices 110, 130, 150 need to communicate to the hub 100 to synchronize their local timer (slave clock) 112, 132 and 152 with the master timer 102. Time synchronization across the network is achieved and maintained by the hub 100 broadcasting the synchronization messages to all client devices, or by two-way time synchronization message exchanging between the hub 100 and client devices. Various off-the-shelf network time protocols such as RBS (Reference Broadcast Time synchronization), NTP (Network Time Protocol) and PTP (Precision Time Protocol) may be implemented to achieve the Time synchronization. With all the client devices and the hub tracking the master timer 102 as the common timing reference, the sport data can be generated and shared in a timing-synchronized fashion across said network.

Based on the data sharing fashions, the client devices can be classified into two categories: producer and consumer. A producer client device setup one or more logical channels with the hub, generates sport data packets and sends them to the hub. Each logical channel carries a specific type of sport data packets from the sending producer client device. A consumer subscribes certain channels from the hub. It receives and processes the sport data packets forwarded by the hub through the subscribed channels. A client device can be both a producer and a consumer.

In FIG. 1, the client device 110 illustrates one embodiment of the producer. The producer can be equipped with data sources represented as 116, 118 and 120. The data sources can be image sensors, audio sensors, GPS/GNSS receivers, accelerometers, gyroscopes, magnetometers and so on. The sensors generate raw data such as image, audio, location or inertial measurements at scheduled periods. The producer can also be equipped with processor 122 take the said raw data as input. Different operations such as filtering, sample rate changing, data reformatting, data compression, data fusion can be done by said processor 122. In addition, the processors 122 can perform certain pattern recognition tasks. For example, processors 122 can detect certain sport related events, such as ball dribbling and scoring, based on the values and timing relationship of said raw data from the sensors. The communication module 114 setup communication data link between the client device 110 and hub 100. The selected raw data from the sensors and processed output of the processor 122 are encapsulated as sport data packets, time stamped by local slave timer 112 and sent to the hub 100.

The client device 130 illustrates one embodiment of the consumer. A consumer receives sports data packets generated by other producer client devices and forwarded by the hub 100. The communication module 134 setup communication data link between the client device 130 and hub 100. Sports data packets of logical channels subscribed by the client device 130 during registration process are forwarded by the hub to the client device 130. The received sport data packets can be timestamped according to the time of the local timer 132 at the reception. The processor 136 performs operations such as filtering, sample rate changing, reformatting, compression, data fusion, pattern recognition on the incoming sports data packets. The output of the processor can be sent to data sinks such as display 138 or data storage 140.

A client device can be both a producer and a consumer at the same time as the client device 150 illustrated. The client device 150 could be equipped with both data sources such as sensor 158 and data sinks such as storage 160. The sport data packets travel on both directions between the client device 150 and the hub 100. The client device 150 can operate as a computing node. In this case, the communication module 152 receives the sport data packets generated by other client devices from the hub 100. The processor 156 performs filtering, sample rate changing, data reformatting, data compression, data fusion, pattern recognition on the incoming sport data packets and generated new sports data packets. Said new sport data packets are sent back to logical channels client device 150 established and later consumed by other client devices.

Before the sport data packets sharing happens among the client devices and a hub 100, one or more logic channels need to be established. Each logic channel carries a specific type of sport data packets. The logic channels are created when the client devices are connected to the hub 100 through a registration procedure. During the registration procedure, a producer client device and the hub 100 negotiate on a list of logical channels the producer client device can establish. The hub 100 saves the list in its database 106. During the registration procedure of a consumer, the consumer first obtains the logical channel list from the hub 100, then subscribe selected logical channels from the list. If the subscription succeeds, the hub 100 will update the routing information in the database 106. The sport data packets sent by the producer through the subscribed logical channels will be routed to the subscribing consumers according the routing information.

Figure 2B:
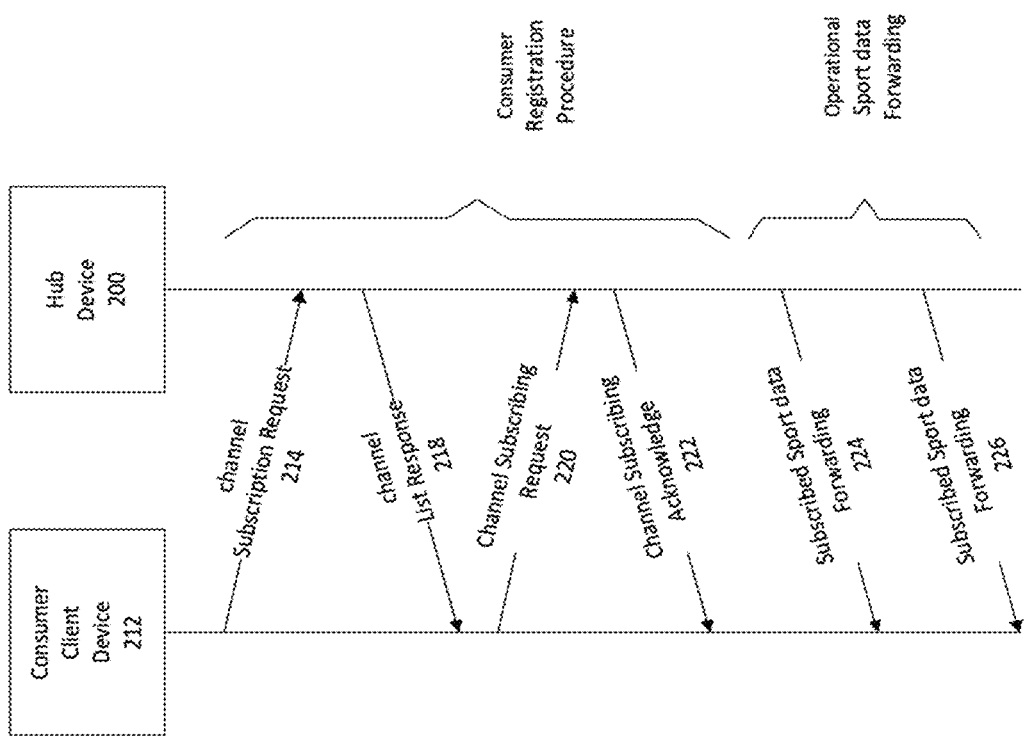
FIG. 2B shows a registration procedure between a consumer client device 212 and the hub 200.
Figure 2A:
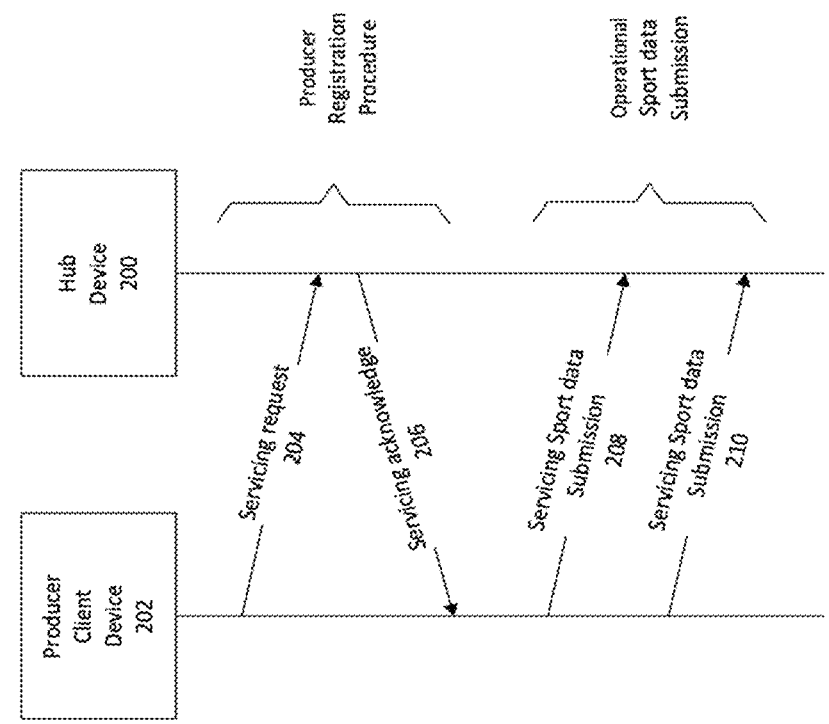
FIG. 2A shows a registration procedure between a producer client device 202 and a hub 200.

FIG. 2A shows the registration procedure between a producer client device 202 and a hub 200. To setup the logic channels to the hub 200, the producer client device 202 first sends a channel setup request 204 to the hub 200. The channel setup request 204 may comprise multiple attributes of the client device 202. Said attributes can be a unique identifier, type and description of the client device 202. Said attributes also include a list of logical channels the client device 202 is capable to setup. Every entry in said list is designated for one logic channel. The entry comprises the logic channel specific parameters such as the type, formats and update periods of the sport data transferred in current logical channel.

The hub 200 responds with the channel setup acknowledgement 206, accepting a subset of said logical channels list. For each logical channel in the list, the acknowledgement 206 may include commands to change some parameters, such as update period. Both the hub 200 and the registering client device will save accepted logical channel list. After establishing the logic channels between the client device 202 and the hub 200, sport data packets generated by the client device 202 can be submit to the hub 200 through the logic channels. The arrows 208 and 210 illustrate the sport data submission.

FIG. 2B shows the registration procedure between a consumer client device 212 and a hub 200. To subscribe logic channels from the hub 200, the consumer client device 212 first sends a channel subscription request 214 to the hub 200. The channel setup request 214 may comprise multiple attributes of the client device 212. Said attributes can include a unique identifier, type and description of the client device 212. hub 200 responses with the Channel List Response 218 comprising a list of established logical channels the client device 212 can choose from. The list of logical channels might be tailored to according the information in the channel subscription request 214. The client device 212 then responds with the Channel Subscribing Request 216, selecting a subset of the logical channel list in the Channel List Response 218. The channel subscription is finally confirmed by the Channel Subscribing Acknowledge 220 from the hub 200. After the 220, the hub 200 will forward the sport data packets it received from subscribed channels to the consumer client device 212. The packet forwarding is illustrated by 222 and 224 in the FIG. 2B.

For client devices act as both producer and consumer, the registration procedure can be accomplished by combining the procedures shown in FIG. 2A and FIG. 2B.

Figure 3:
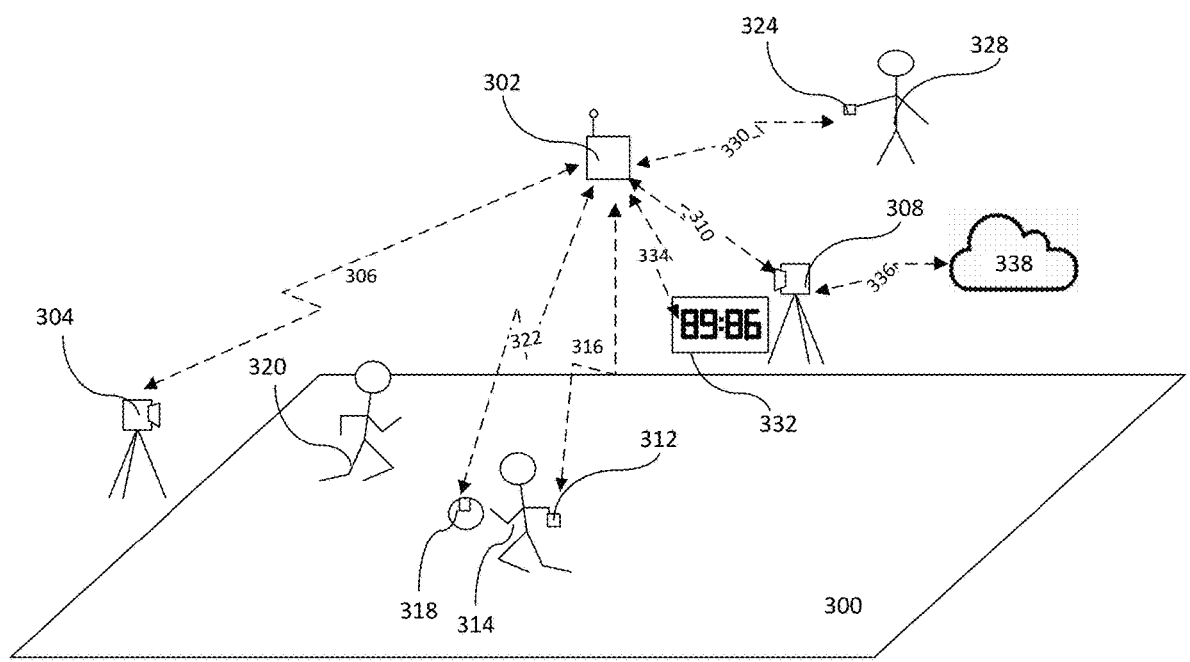
FIG. 3 illustrates a user scenario of the present invention.

FIG. 3 illustrates a user scenario of the present invention. The Scalable Network is deployed at the sport activity scene 300 where sport games, events or practicing session is held.

In one embodiment, the producer client device 312 is a wearable sensor device attached to the body or the sports apparel of player 314 who is participating the sports activity. The client device 312 is equipped with sensors to measure the location, speed, acceleration, orientation of the player 314. the client device 312 can also be configured to measure data from its environment, such as temperature and audio signature. By analyzing the dynamics of the measurements, a processor in the client device 312 can identify specific sport events, such as dribbling, passing and score attempts and so on. In addition, the client device 312 can be equipped with a user interface through which the wearing player can provide his or her user input in real time. The information of measurement data and identified sport events are time stamped according the local time reference and encapsulated into the sport data packets. The sport data packets are sent to the hub 302 over the wireless link 316 established between the client device 312 and the hub 302.

In another embodiment, the producer client devices 318 are designed to attach to the sports equipment such as the game balls. The client device 318 is equipped with sensors to measure the location, speed, acceleration, orientation of the attached sport equipment. By analyzing the dynamics of the measurements, a processor in the client devices 318 can identify specific sport events, such as dribbling, passing and score attempts. The information of measurement data and identified sport events are time stamped according the local time reference and encapsulated into the sport data packets. The sport data packets are sent to the hub 302 over the wireless link 322 established between the client device 318 and the server 302.

In yet another embodiment, the producer client device 304 is equipped with one or more image sensors and an image processor. Said image processor analyze the images captured by the image sensors at the sport scene 300 and monitor the parameters such as locations, moving speeds, trajectory s and gestures of the players and sport equipment. By analyzing the dynamics of the parameters, the image processor can identify specific sport events, such as dribbling, passing, score attempts and confirmed scores. Information of said parameters and identified sport events are time stamped and encapsulated into the sport data packets, then send to the hub 302 though the wired or wireless link 310 established between the client device 304 and hub 302.

In one embodiment, the consumer client devices 308 is equipped with camera. The client devices 308 generates the video and audio footages of sport scene 300 and saves them to the media file in the local storage. The media file is structured so that the video and audio footages are save in the data tracks. The network time values are periodically saved as timed metadata into the structured data boxes or separated data track of the media file. The client device 304 accepts certain sport event data packets from the hubs 302, the event data packets may represent dribbling, passing, score attempts and confirmed scores. The timestamp of the received sport event data packets and the timed metadata of the local media file was generated with respect of the common time reference: the master timer of the hub 302, so they can be correlated to find out the portions of media file saved at the time said sport event data packets was generated. Highlight media clips may be tailored from the media file based on the correlation. The highlight media clips and sport data packets subscribed can be buffered by client device 304 and uploaded to the servers on the internet 338 though a wired or wireless data link 336 through an Internet Service Provider during or after the sports events.

A software application in the smart phone 324 implements the functionality of either consumer or producer or both. The smart phone 324 is controlled by the event participator 328. In cases that the participator 328 is a sport official, such as a referee or a scorekeeper, the smart phone 324 can be used as a sport statistics input device. The software application encapsulates sport statistics inputs such as score numbers and foul information into the sport data packets and sends the packets to the hub 302. The hub 302 forward them to anther consumer client devices 332 act as a scoreboard for sport statistics display. In other cases that the participator 328 is a coach or an audience, smart phone 324 can act as a consumer client device to subscribe and view specific sports data generated within the scalable network, such as game statistics or Highlight media clips of individual players.

Figure 4A:
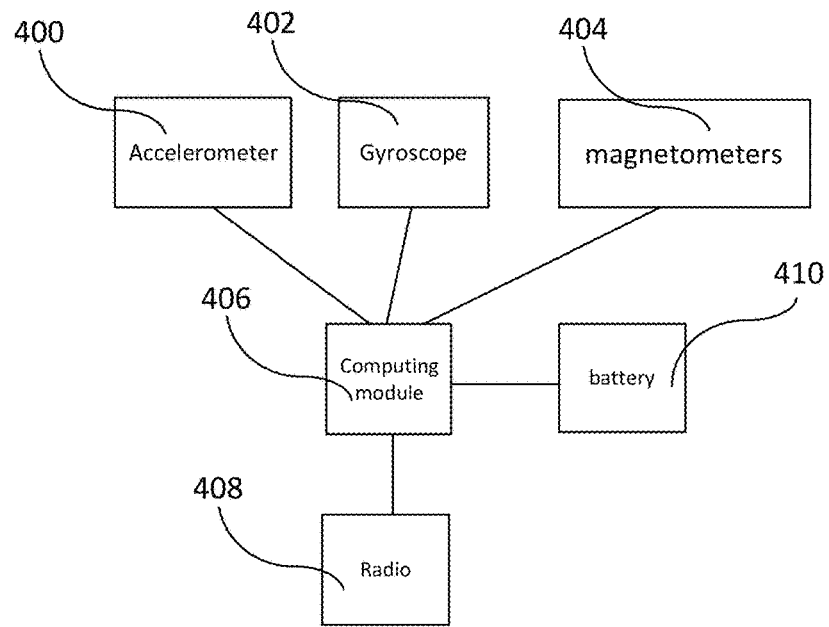
FIG. 4A presents a detailed block diagram of the client device 312.

FIG. 4A presents a detailed block diagram of the client device 312 of FIG. 3. The sensor module includes a computing module 406, a battery 410, a radio 408 and a plurality of sensors such as accelerometer 400, the gyroscope 402 and magnetometers 404 and so on. In this embodiment, the sensor modules are made wearable and attached to the wrist of a player. Various motion measurements such as moving speed, rotating speed, moving direction and acceleration can be collected by the sensors. The collected sensor measurements are fed into the computing modules 406. The outputs of the computing modules 406 are sent to the hub by the radio 408. The battery 410 supply power to the system.

Figure 4B:
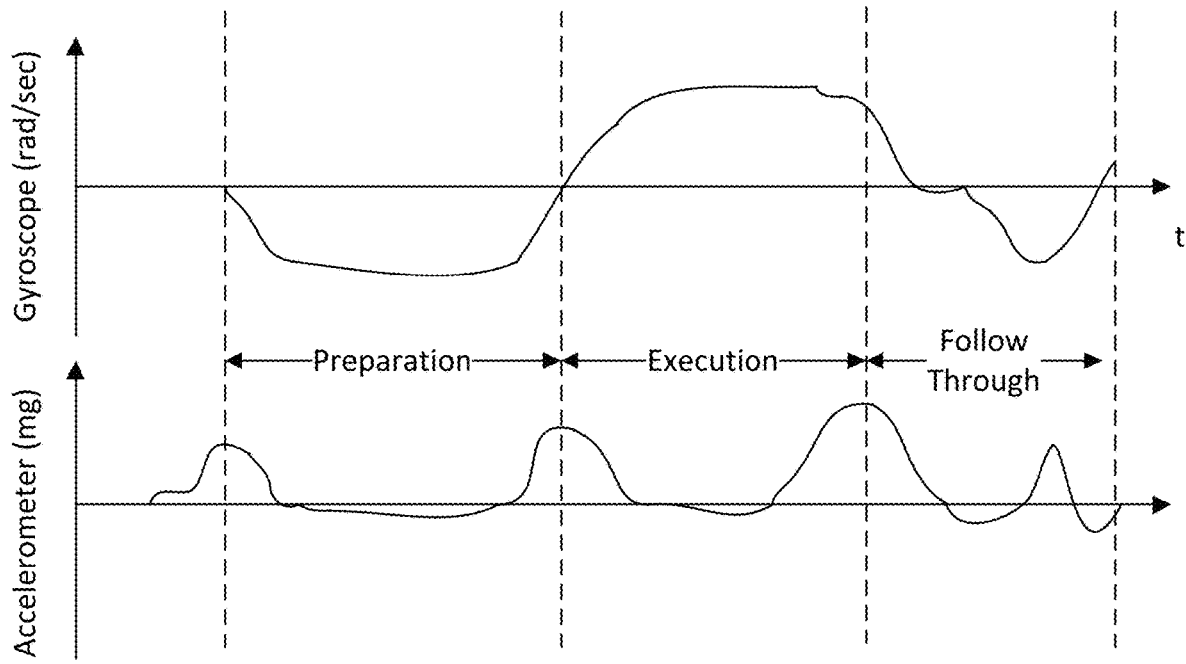
FIG. 4B illustrates an example of the sports event identification by the computing modules 406.

FIG. 4B illustrates an example of the sports event identification by the computing modules 406. The "Preparation-Execution-Follow through" pattern can be identified by certain machine learning algorithms implemented in the computing module 406 and the player's movement can be classified as a ball shooting event. Likewise, other feature movements such as dribbling and passing can also be detected by the computing module 406, and corresponding sports data packets can be generated.

Figure 5:
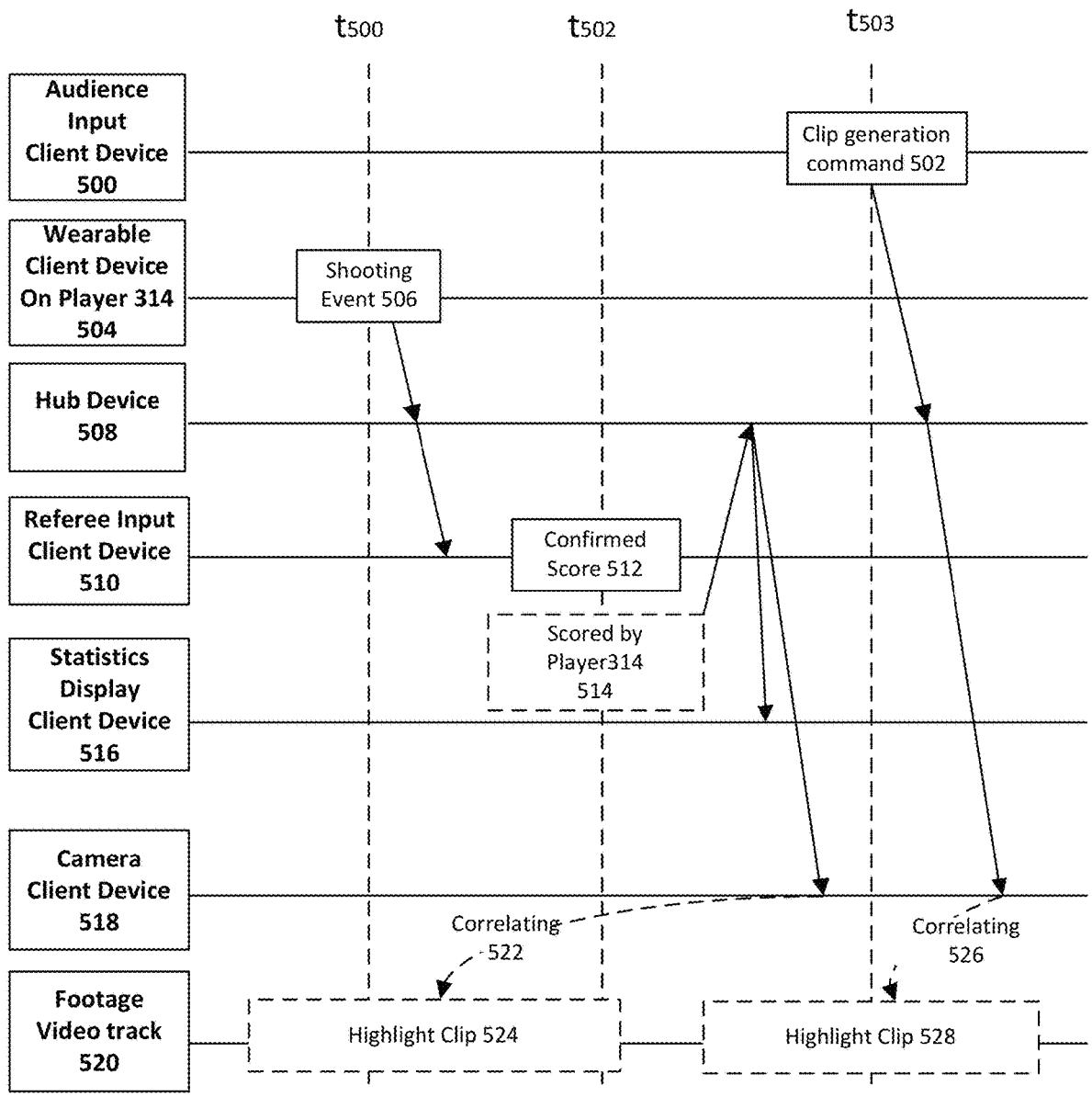
FIG. 5 illustrates an exemplary timing diagram of the joint sport event detection and sport data generation within the scalable network.

FIG. 5 illustrates an exemplary timing diagram of the joint sport event detection and sport data generation within the scalable network. The client devices 500, 504, 510, 516 and 518 are connected to the hub 508 via wired or wireless data links. The local time of the client devices are synchronized to the network time distributed by the hub 508 using certain network time protocol. The wearable sensor client device 504 is also represented as 312 in FIG. 3. It is attached to the wrist of one of the players 314 in FIG. 3 and detects a shooting event 506 at the network time t500. The client device 504 encapsulates the information of the shooting event 506 and the time stamp of t500 into a sport data packet and sends it to the hub 508. The hub 508 is also represented as 302 in FIG. 3. It forwards said sport data packet to a referee input client device 510, which subscribed the logical channel carrying the shooting events. The referee input client device 510 is also represented as 324 in FIG. 3. The referee generates the score confirming event 512 though the user interface of client device 510 at network time t502. If certain criteria is fulfilled, for example the time difference between the t502 and t500 are under certain threshold, the client device 510 may reason from the events 506 and 512 that the confirmed score are made by the player 314 and generate another event 514 accordingly. The event 514 is enclosed in a box with dash line to show the significance that it was generated by combining data from different client devices in the network.

Next, the event 514 as well as the time stamps of t500 and t502 are encapsulated into a sport data packet. The sport data packet is forwarded by the hub 508 to its subscriber, namely Statistics Display client device 516 and Camera client device 518. client device 516 is also represented as 332 in FIG. 3. It updates its display according the information of the event 514. The Camera client device 518 is also represented as 308 in FIG. 3. It generates video footage of the sport scene and stream the video footage to the video track 520 of a media file in the local storage on the client device 518. Timed metadata synchronized with network time is saved along the video footage. When the camera client device 518 receives the sport event 514 in a sport data packet, correlating operation 522 can be done to locate the portion of said video footage taken around the system time t500 and t502. Said portion of the video footage can be extracted to serve as the highlight clip 524 of the score event 514.

The correlating operation and highlight clip generation can be triggered by other sport event data packets, such as a user input from the Audience input client device 500. When the audience decides to capture the highlight of the game around t502, a clip generation command is created at the client device 500 and forwarded to the Camera Client Device 518 by the hub 508. The correlating operation 526 locates the portion of video footage saved by Client Device 518 around t502 and extract it as the highlight clip 528.

Figures 6A, 6B:
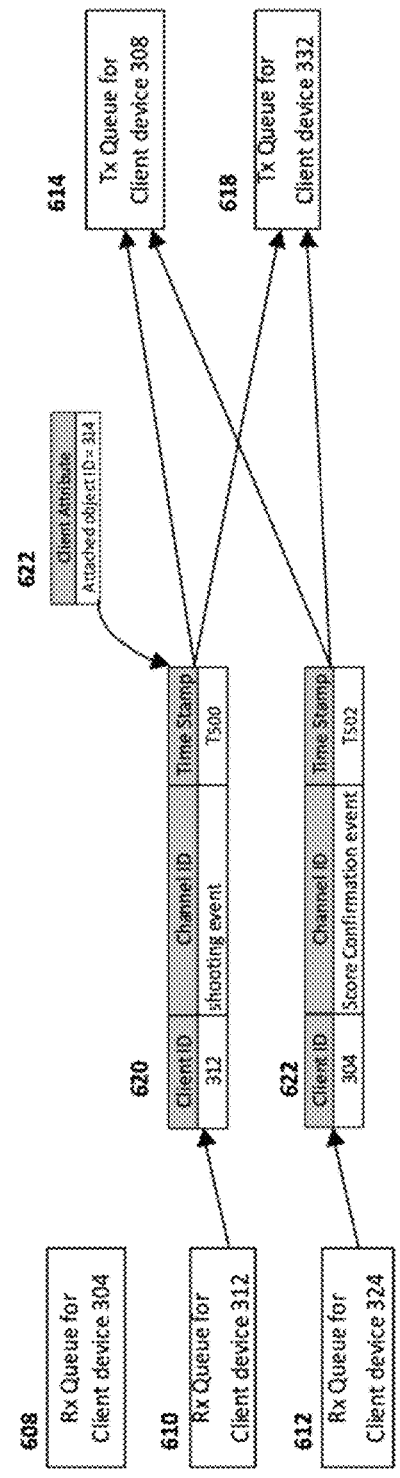
FIG. 6A illustrates the database structures of a preferred embodiment of the hub.
FIG. 6B demonstrates the sport data packets forwarding in the hub.

FIG. 6A illustrates the database structures of a preferred embodiment of the hub. The hub maintains database tables: Device Registration Table 600, Channel Registration Table 602 and Channel Subscriber Table 604. When client devices join and register to the network, a new entry will be added to the client registration table 600. The entry includes fields such as client device ID, client device type and multiple client device attributes. The client device ID uniquely identifies each client device in the network. It could be hard coded during the manufacturing or assigned by the hub during the registration procedure. For simplicity, the client device notion numbers in the FIG. 3 are used for their client ID in FIG. 6. The client device type classifies the client devices according to their functionalities. Each client device can have multiple attributes in the table 600. For example, if the client device is stationary, it may have an attribute of its physical location; If the client device is a wearable sensor device, it should have an attribute identifying the sport participator it is attached on.

During registration, one or multiple entries can be added to the Channel Registration Table 602 for each producer client devices. Each entry in table 602 represents one logical channel. The mandatory fields of the table should include the producer client device ID and the channel ID. The producer client device ID field is same as the client device ID in table 600, it identifies the data source of the current logical channel. The channel ID together with the client device ID uniquely identifies the logical channel in the table 602. The channel ID could be a string or a pre-assigned sequence number. Each entry in the table 602 may have one or more attributes defining the format the sport data packet transferred in the current logical channel. A "channel index" field may be added to the table 602 to serve as a primary key to index all existing logical channels, that means each entry in the table 602 has a unique channel index.

When a consumer client device joins the network, it first requests a logical channel list from the hub. The hub tailors the information from the table 602 to form a dedicated channel list for said consumer client device. The consumer client device, in turn, will subscribe a subset of the dedicated channel list. If accepted by the hub, for each subscribed channel, the hub will add an entry to the Channel Subscriber Table 604. The "channel index" field in Table 604 serves as foreign key to create links between entries in Table 602 and 604. The links are illustrated as dash arrow lines in FIG. 6A. The "subscriber client ID" field indicates the data packet destinations of current logical channel.

When a client device disconnects from the network, the hub will delete all entries with the client ID and associated channel IDs of this client device from the table 600, 602 and 604.

FIG. 6B demonstrates the sport data packets forwarding in the hub. The hub setup a receiving queue for each connected producer client device and a transmitting queue for each connected consumer client device. For example, the receive queue 610 is designated to the client device 312, the sport data packets generated from client device 312 are received and buffered in the receive queue 610 before routed to their subscribers. The sport data packet 620 is currently in the receiving queue 610 and sport data packet 622 is currently in the receiving queue 612. Use the client ID and Channel ID fields of the sport data packets, the hub can first locate the channel entries related to the packets in the table 602, then find the subscriber client IDs from the table 604. For example, the producer client ID and the Channel ID of the packet 620 matches the fourth entry in the table 602 with Channel Index equal to 3. Using the channel index of 3 as foreign key to search the table 604, the hub can find the subscriber Client ID 308 and 332. Before the sport data packet is forwarded to the transmitting queue of the subscriber Clients, the hub can attach additional information from its database such as certain attribute of the source client. For example, the "attached object ID" attribute 622 is retrieved from the Client Registration Table 600 and added to the shooting event packet 620. It will help the subscriber to identify the player who has made the shooting attempt.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

The invention claimed is:

1. A scalable sport data collecting, sharing and processing system comprising: a hub device, and a plurality of client devices, each client device being connected to the hub device via a data communication link, wherein the client devices include a producer client device and a consumer client device; wherein the producer client device includes one or more sensors selected from the group consisting of an image sensor, an audio sensor, a GPS/GNSS receiver, an accelerometer, a gyroscope, and a magnetometer, a processor, and a communication module; and wherein the consumer client device includes a process, a communication module, a display and a data storage; wherein the huh device establishes a centralized local network; wherein the hub device includes a master timer, and the client, devices each have a local timer that synchronizes with the master timer; and wherein a time synchronization is achieved and maintained by two-was-time synchronization messages exchanging between the hub and the client devices.

2. The scalable sport data collecting, sharing and processing system of claim 1, wherein the producer client device generates and sends sport data packets to the hub; and the consumer client device receives and processes the sports data packets forwarded by the hub.

3. The scalable sport data collecting, sharing and processing system of claim 1, wherein the data communication link includes a data sharing logical channel, and the client devices are adapted for exchanging sport data with each other using the hub device as a router.

4. The scalable sport data collecting, sharing and processing system of claim 1, wherein the producer client device is a wearable sensor device that include sensors to measure the location, speed, acceleration, orientation of a wearing player.

5. The scalable sport data collecting, sharing and processing system of claim 4, wherein the wearable sensor device further includes a computing module, a battery, and a radio, and the sensors of the wearable sensor device include an accelerometer, a gyroscope, and a magnetometer.

6. The scalable sport data collecting, sharing and processing system of claim 1, wherein the producer client device is a device attached to a sport equipment that includes sensors to measure the location, speed, acceleration, orientation of the sport equipment.

7. The scalable sport data collecting, sharing and processing system of claim 1, wherein the producer client includes one or more image sensors and an image processer.

8. The scalable sport data collecting, sharing and processing system of claim 1, wherein the producer client includes a camera.

9. The scalable sport, data collecting, sharing and processing system of claim 1, wherein the client devices are a smart phone.

10. The scalable sport data collecting, sharing and processing system of claim 1, wherein the data communication link between the producer client device and the hub device comprises: sending a channel setup request from the producer client device to the hub, acknowledging the channel setup request by the hub, and sending sport data packets front the producer client device to the hub.

11. The scalable sport data collecting, sharing and processing system of claim 1, wherein the data communication link between the consumer client device and the hub device comprises: sending a first channel subscription request from the consumer client device to the hub, sending a channel list by the hub to the consumer client device, sending a second channel subscription request from the consumer client device to the hub, acknowledging the second channel subscription request by the hub, and sending sport data packets from the hub to the consumer client device.

12. The scalable sport data collecting, sharing and processing system of claim 1, wherein the hub comprises a database that includes client registration information, channel registration information, and channel subscriber information.

13. The scalable sport data collecting, sharing and processing system of claim 12, wherein the hub receives spoil data packets from the producer client device, locates corresponding channel subscriber information, attaches additional information to the sport data packets from the database, and forwarding the sport data packets to the consumer client device.

14. The scalable sport data collecting, sharing and processing system of claim 1, wherein the scalable sport data collecting, sharing and processing system comprises: an audience input client device, a wearable client device, a hub device, a referee input client device, a statistics display client device, and a camera client device; and the wearable client device generate sport data packets, the consumer client or the hub detects sports events by correlating the sport data packets, and the sport events are saved locally or encapsulated in new sport data packets and sent to the hub device.

15. The scalable sport data collecting, sharing and processing system of claim 14, wherein the hub device correlates the sport data packets with a first video clip recorded by the camera client device.

16. The scalable sport data collecting, sharing and processing system of claim 14, wherein the audience input client device generates a clip generation command, and the hub device correlates the clip generation command with a second video c recorded by the camera client device.

17. The scalable sport data collecting, sharing and processing system of claim 1, wherein the producer client device generates sport data packets, the sport data packets encapsulate data collected from the sensors and a timestamp indicating the producer client device's local timer value when the sport data packets are generated; and wherein the sport data packets are generated periodically or when the producer client device detects certain events.

* * * * *